(12) United States Patent
Nieminen et al.

(10) Patent No.: US 7,353,125 B2
(45) Date of Patent: Apr. 1, 2008

(54) EDDY CURRENT DETECTION AND COMPENSATION

(75) Inventors: John M. Nieminen, Waterloo (CA); Stefan R. Kirsch, Radolfzell (DE)

(73) Assignee: Northern Digital Inc., Waterloo, Ontario ( * ) Notice: Subject to any disclaimer, the term of this patent is extended or adjusted under 35 U.S.C. 154(b) by 0 days.

(21) Appl. No.: 11/331,518

(22) Filed: Jan. 13, 2006

(65) Prior Publication Data

US 2006/0116832 A1   Jun. 1, 2006

Related U.S. Application Data

(62) Division of application No. 10/824,846, filed on Apr. 15, 2004.

(60) Provisional application No. 60/463,576, filed on Apr. 17, 2003.

(51) Int. Cl.
 *G01R 13/00* (2006.01)
(52) U.S. Cl. ..................................... 702/69
(58) Field of Classification Search ................ 702/69
 See application file for complete search history.

(56) References Cited

U.S. PATENT DOCUMENTS

| 4,829,250 A | 5/1989 | Rotier |
| 5,629,626 A * | 5/1997 | Russell et al. ............. 324/345 |
| 5,767,669 A | 6/1998 | Hansen et al. |
| 6,172,499 B1 | 1/2001 | Ashe |
| 6,427,079 B1 | 7/2002 | Schneider et al. |
| 6,624,626 B2 | 9/2003 | Khalfin |
| 2005/0222625 A1* | 10/2005 | Laniado et al. ............ 607/2 |

FOREIGN PATENT DOCUMENTS

| EP | 0 228 056 | 8/1987 |
| EP | 0 993 804 A1 | 4/2000 |
| EP | 1203560 | 5/2002 |
| EP | 1203560 A2 | 5/2002 |
| WO | 02/08793 | 1/2002 |

OTHER PUBLICATIONS

International Search Report, PCT/CA2004/000587, dated Aug. 23, 2004, 3 pages.

* cited by examiner

*Primary Examiner*—John Barlow
*Assistant Examiner*—Aditya S. Bhat
(74) *Attorney, Agent, or Firm*—Fish & Richardson P.C.

(57) ABSTRACT

A distortion compensation method includes determining an undisturbed phase for at least one of a first position indication signal and a second position indication signal. The method includes determining an undisturbed ratio that relates the amplitude of the first position indication signal at a first frequency to the amplitude of the second position indication signal at a second frequency. The method also includes determining a disturbed amplitude of the position indication signal and adjusting a position indication based on the disturbed amplitude and phase, the undisturbed amplitude ratio, and the undisturbed phase. The method further comprises determining a relationship between the eddy current phase of the first position indication signal and the second position indication signal.

15 Claims, 11 Drawing Sheets

EDDY CURRENT DETECTION AND COMPENSATION

This application is a divisional application of and claims priority under 35 U.S.C. §120 to application Ser. No. 10/824,846, filed Apr. 15, 2004, which claims the benefit of U.S. Provisional Application No. 60/463,576, filed Apr. 17, 2003. Each of these patent applications is incorporated herein by reference.

BACKGROUND

Magnetic tracking systems are used in variety of applications, for example in image guided medical applications, radiation therapy (e.g. tumor tracking), other medical diagnostic and therapeutic devices, ergonomics and human motion research, animation (e.g. motion capture), and industrial measuring. The presence of conductive objects in the vicinity of the magnetic tracking system can degrade the performance of the system. The eddy currents induced within a conductive object can disturb the position indication of a sensor and result in inaccurate position and/or orientation information.

SUMMARY

In one aspect of the invention, a distortion compensation method includes determining an undisturbed phase for at least one of a first position indication signal and a second position indication signal. The method includes determining an undisturbed ratio that relates the amplitude of the first position indication signal at a first frequency to the amplitude of the second position indication signal at a second frequency. The method also includes determining a disturbed amplitude of the position indication signal and adjusting a position indication based on the disturbed amplitude and phase, the undisturbed amplitude ratio, and the undisturbed phase. The method further comprises determining a relationship between the eddy current phase of the first position indication signal and the second position indication signal.

In another aspect of the invention, a method for detecting the presence of conductive objects includes determining a characteristic frequency function of a magnetic tracking system and measuring a disturbed frequency function. The method also includes calculating a chi-squared value based on the characteristic undisturbed frequency function and the disturbed frequency function and monitoring the chi-squared value to detect changes indicating the presence of a conductive object.

In a further aspect of the invention, a method includes measuring characteristics of a conductive object and determining an eddy current phase based on the characterization. The method also includes measuring a disturbed amplitude and calculating an undisturbed (i.e. corrected) amplitude based on the eddy current phase, an undisturbed sensor phase, and the disturbed amplitude.

Embodiments of the above aspects can include one or more of the following features.

A second undisturbed ratio can be determined that relates the amplitude of either of the first and the second position indication signals to the amplitude of a third position indication signal at a third frequency. A relationship between the eddy current phases of either the first or second position indication signal and the third position indication signal can be determined and the position indication can be adjusted.

The first frequency can be a superior harmonic of the second position indication signal and the second frequency can be a subordinate harmonic of the first position indication signal. For example, the superior harmonic can be the fundamental frequency and the subordinate harmonic can be the third harmonic. In some embodiments, the first frequency is less than the second frequency. The first frequency and the second frequency can be harmonically related. Multiple frequencies can be generated by a chirped waveform, for example. Other aspects of the invention can include receiving from a sensor the real and imaginary components of the first and second position indication signals.

The distortion compensation method can be repeated for a plurality of position indication signals. The method can be used for detecting the presence of eddy currents in a conductive object. Detecting the presence of an eddy current can include monitoring a ratio of the amplitude of the first position indication signal and the amplitude of the second position indication signal. In another example, detecting the presence of an eddy current can include detecting a change in the undisturbed phase. In another example, detecting the presence of an eddy current can include detecting changes in characteristics of undisturbed real and imaginary components of a position indication signal.

Determining the undisturbed phase can include measuring asymptotic phase values and using the asymptotic phase values to calculate the undisturbed phase. Determining the undisturbed phase can alternately or in addition include iteratively calculating phase values and adjusting an asymptotic phase value. Calculating the eddy current phase can include using a numerical method to solve a set of equations or using a closed form solution to solve a set of equations.

In some examples, the method can include monitoring the chi-squared value for a plurality of position indication signals. The method can also include setting thresholds for the chi-squared value to indicate different levels of distortion. Detecting a change in the chi-squared value of a position indication signal can indicate the presence of conductive objects. The detection of a change in a chi-squared value at a particular frequency range (e.g., a mid-frequency range, a low-frequency range, or a high-frequency range) can indicate the presence of a particular type of conductive object.

Among other advantages, the eddy current compensation provides a real-time determination of the eddy current phase and amplitude. The method provides compensation for a position indication to account for the eddy current generated by a conductive object.

Among other advantages, in some embodiments, the use of multiple field generator coils provides the advantage of increased sensitivity and redundancy. The presence of conductive objects can cause a signal disturbance due to coupling to one or more of the field generator and/or sensor coils.

DESCRIPTION

Figure 1:
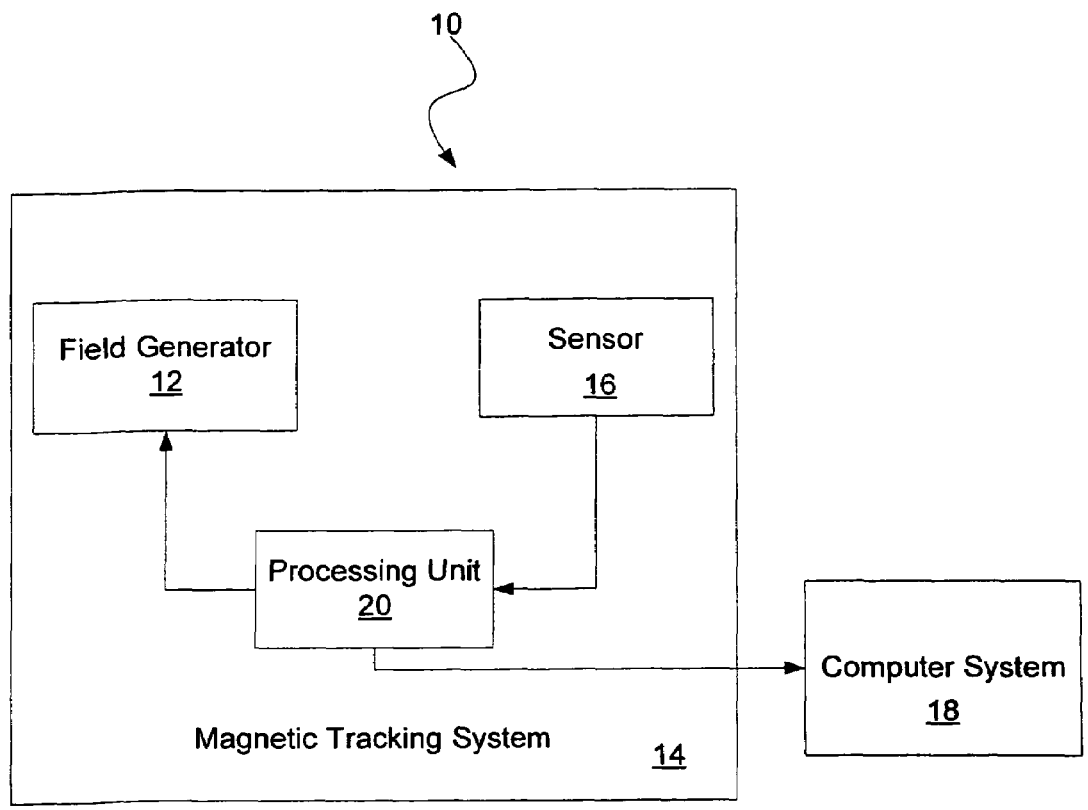
FIG. 1 is a block diagram of a coordinate measurement system.

Referring to FIG. 1, a coordinate measurement system 10 includes a magnetic tracking system 14 having one or more sensors 16. Magnetic tracking systems (also referred to as coordinate measurement systems) are susceptible to distortions (also referred to as disturbances) due to eddy currents resulting from the presence of conductive materials in or near the sensor 16 and/or the field generator 12. Examples of conductive materials include metals (e.g. stainless steel), carbon fiber, and certain conductive plastics. The electromagnetic coupling that generates eddy currents is dependent on the frequency of a transmitted AC magnetic field. In addition, eddy currents are phase shifted with respect to the magnetic tracker source drive current that generates the magnetic field.

In order to accurately provide a position indication, the magnetic tracking system includes a field generator 12 that generates an input signal having two or more frequency components. The lowest of these frequency components is termed the fundamental frequency. For example, a typical fundamental frequency might be 1000 Hz. Additional frequency components could be harmonics of the fundamental frequency, or could be other non-harmonic frequencies. Examples of waveforms input by the signal input include a square wave, a triangular wave, a sawtooth wave (e.g. ramp), a sinusoidal wave, a chirped wave, a multiple frequency waveform of any kind, or any combination of these.

Properties of the eddy currents generated by the presence of conductive objects near the magnetic tracking system 14 depend on the excitation frequency and the coupling of the transmitted AC magnetic field. A computer system 18 or other computational unit analyzes the position indication signals generated at multiple frequencies. Based on the position indication signals, computer system 18 calculates the eddy current phase and amplitude and compensates the position indication to remove the measurement error induced by the eddy current.

Figure 2:
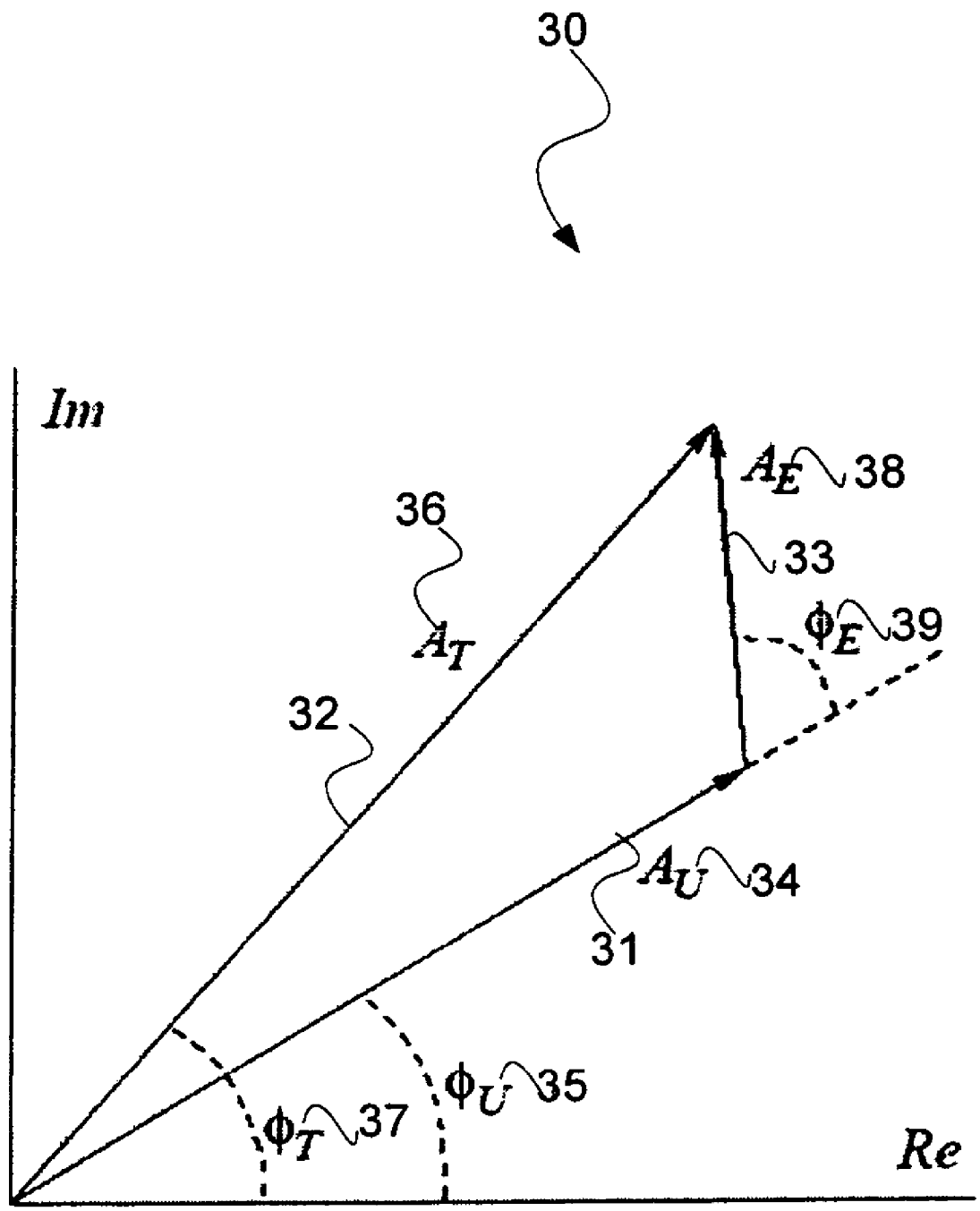
FIG. 2 is a phasor diagram including an undisturbed phasor, a disturbed phasor, and an eddy current phasor.

Referring to FIG. 2, a graphical representation 30 of the undisturbed phasor 31, disturbed or total phasor 32, and eddy current phasor 33 is shown. Each phasor is represented by an amplitude (A) and a phase (ϕ). For example, the undisturbed phasor 31 is represented as an undisturbed amplitude ($A_U$) 34 and an undisturbed phase ($\phi_U$) 35, the disturbed or total phasor 32 is represented as a disturbed or total amplitude ($A_T$) 36 and a disturbed or total phase ($\phi_T$) 37, and the eddy current phasor 33 is represented as an eddy current amplitude ($A_E$) 38 and an eddy current phase ($\phi_E$) 39. The disturbed or total phasor 32 is the vector sum of the undisturbed phasor 31 and the eddy current phasor 33. The system uses values of $A_U$ to calculate position indications. This is because the underlying field model used for the position fit is based on the undisturbed fields.

Figure 3:
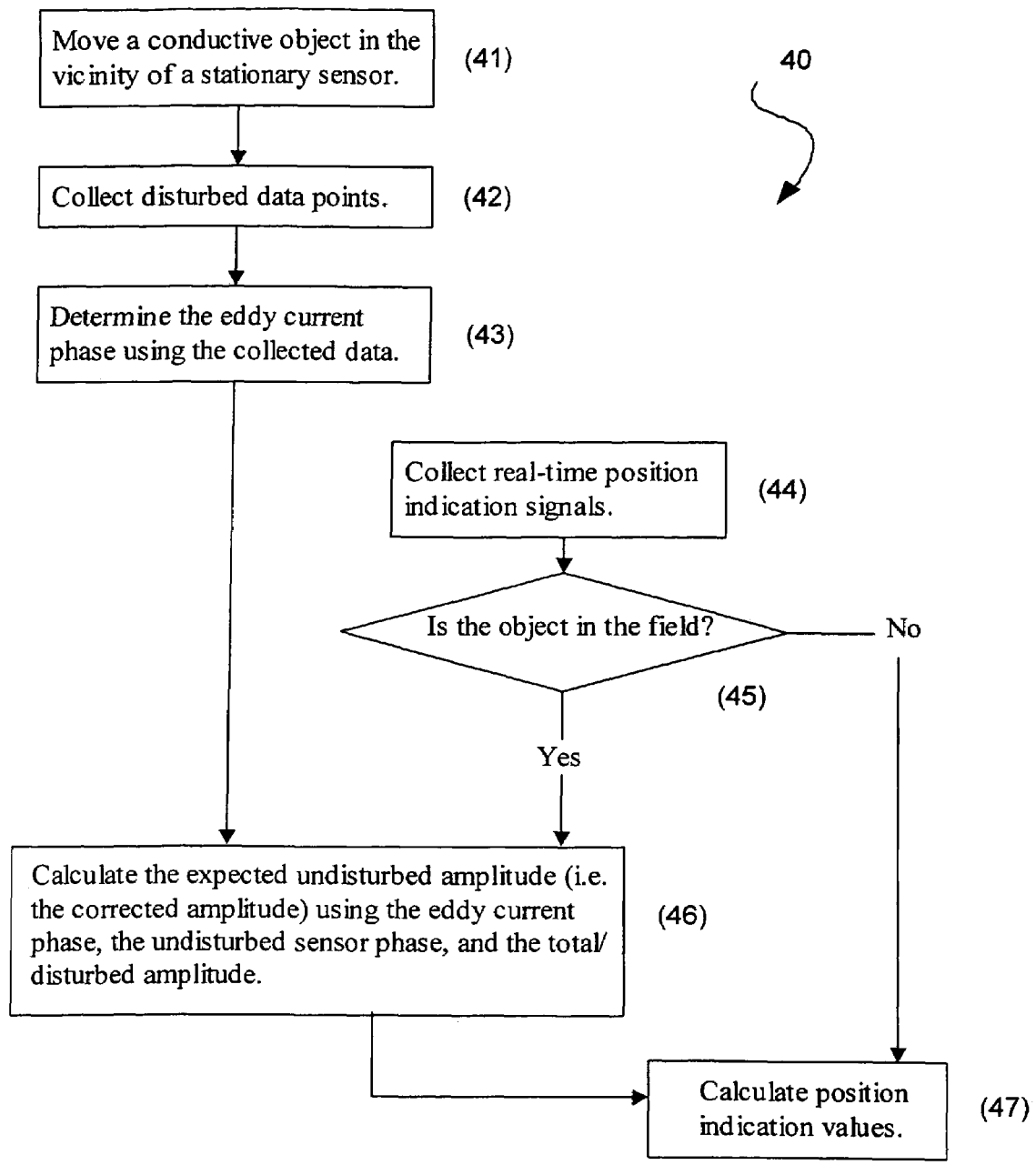
FIG. 3 is a flow chart of a signal compensation process.

Referring to FIG. 3, a process 40 to provide compensation to the disturbed signal is shown. The eddy current amplitude and phase can be calculated and removed from the disturbed phasor 32 leaving the undisturbed phasor 31. The process involves two stages. In the first stage (steps 41, 42, and 43), a given conductive object is characterized by introducing it into the field (step 41) and collecting disturbed signal measurements (step 42). At the time of characterizing a conductive object, $A_U$ and $\phi_U$ are known values and can therefore be used, along with the disturbed data, to determine the eddy current phase (step 43). Details of step 43 are given below. The second stage of process 40 (steps 44, 45, 46, and 47) deal with eddy current compensation during real-time collection of position indication signals (step 44). The eddy current phase ($\phi_E$) of step 43 and the position indication signals of step 44 are used as input to the compensation procedure (step 46) if the characterized conductive object is known to be in the field (step 45). Otherwise, compensation is not necessary and the process goes directly to step 47. Details of the compensation procedure are given below.

Figure 4:
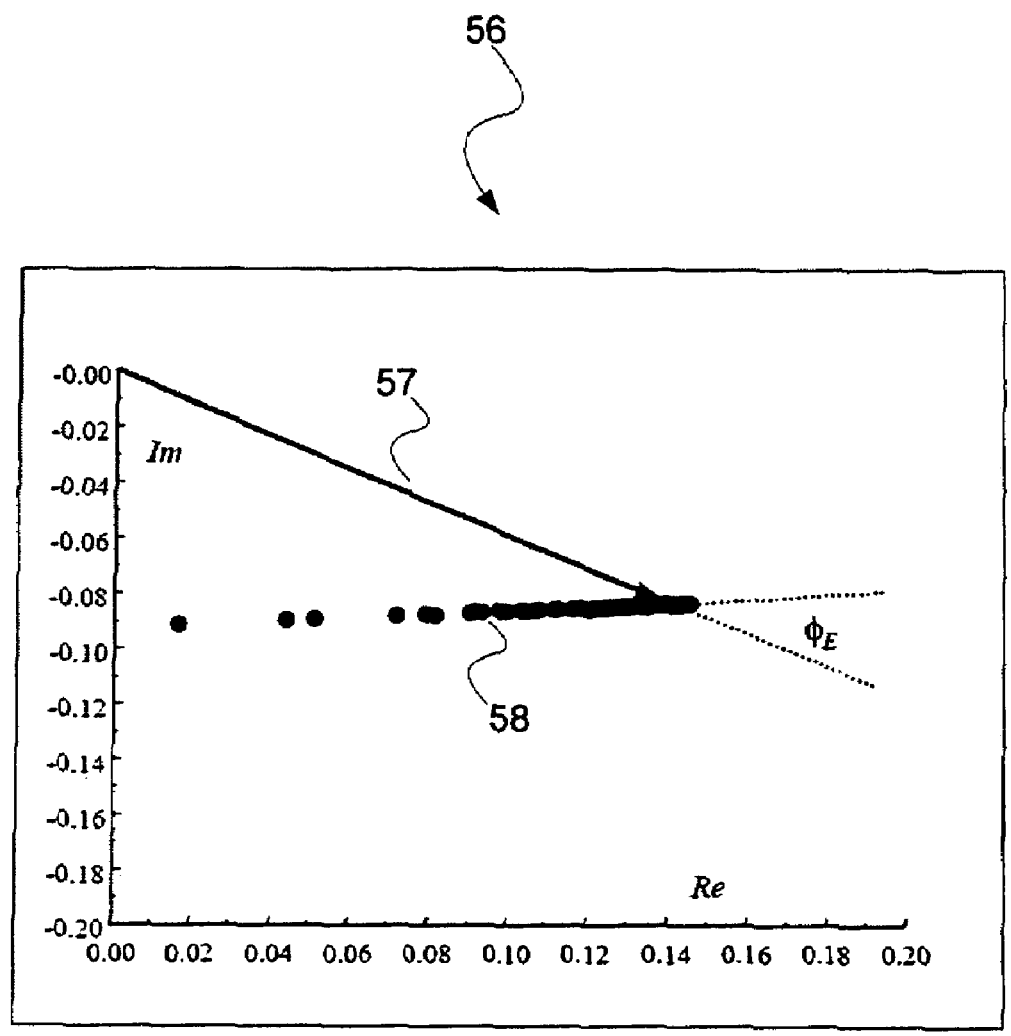
FIG. 4 shows experimental results, used for determining $\phi_E$, when a stainless steel ring is moved in the vicinity of the system of FIG. 1.

Referring to FIG. 4, a graph 56 displays the results of a stationary sensor when a stainless steel ring is randomly waved in the vicinity of a sensor. Graph 56 shows the real and imaginary components of the total sensor signal (solid circles 58) and the undisturbed phasor 57. These results show that for the selected stainless steel ring, $\phi_E$ is a constant. In general, for conductive objects having simple geometric shapes, $\phi_E$ is a constant that depends on the driving frequency of the field generator.

The real and imaginary components of the disturbed/total signal can be expressed as follows:

$$x = Re_T = A_U \cos(\phi_U) + A_E \cos(\phi_U + \phi_E) \quad (1)$$

$$y = Im_T = A_U \sin(\phi_U) + A_E \sin(\phi_U + \phi_E) \quad (2)$$

Using the real and imaginary components of the disturbed/total signal, a chi-squared ($\chi^2$) value can be calculated. To calculate a chi-squared value, equation (1) is solved for $A_E$ and substituted into equation (2). The chi-squared value is defined as follows:

$$\chi^2 = \sum_{j=1}^{N} \left( \frac{y_j - y(x_j; \phi_E)}{\sigma} \right)^2 \quad (3)$$

$$\chi^2 = \sum_{j=1}^{N} \left( \frac{y_j - [A_U \sin\phi_U + (x_j - A_U \cos\phi_U)\tan(\phi_U + \phi_E)]}{\sigma} \right)^2 \quad (4)$$

In equation (3) and equation (4), the measurement uncertainties $\sigma_j$ have been set to σ for simplicity and N is the total number of points collected. In order to determine the eddy current, the derivative of the chi-squared value is calculated and used to determine a minimizing condition as shown in equations (5-9).

$$\frac{\partial \chi^2}{\partial \phi_E} = 0 \quad (5)$$

Substituting the $\chi^2$ equation, taking the derivative, and solving for $\tan(\phi_U + \phi_E)$ results in the equation below:

$$\tan\gamma = \frac{\sum_{j=1}^{N}(y-\alpha)(x_j-\beta)}{\sum_{j=1}^{N}(x_j-\beta)^2} \quad (6)$$

where $$\gamma = \phi_U + \phi_E \quad (7)$$

$$\alpha = A_U \sin\phi_U \quad (8)$$

$$\beta = A_U \cos\phi_U \quad (9)$$

Since magnetic tracking systems often include multiple (e.g., 4, 8, 10) field generator coils, it may be advantageous to calculate $\phi_E$ using data gathered simultaneously from the multiple coils. However, when data is gathered from multiple coils, a closed form solution as shown above may not exist. If a closed form solution does not exist (or is not readily known), the equations can be solved using a numerical method. For example, the equations could be solved using the Levenberg-Marquardt method.

As was the case in the above example, for simple objects the eddy current phase ($\phi_E$) is a constant. However, for more complex objects the eddy current phase ($\phi_E$) may not be constant. The eddy current phase ($\phi_E$) for complex objects often varies depending on the position and the orientation of the distorter. In situations where the eddy current phase varies, the system utilizes a ratio of eddy current phases at different frequencies, as described below in equations (10-14).

The eddy current phase ($\phi_E$) relative to the sensor phase can be written in terms of the inductance and resistance of the distorting object. The inductance and resistance of an object are material constants and do not generally depend on the frequency. The eddy current phase can be defined as follows:

$$\phi_E(\omega) = \frac{\pi}{2} - \arctan\left(\frac{\omega L}{R}\right) \quad (10)$$

where $\omega$ is the angular frequency (i.e., $\omega=2\pi f$). The eddy current phase of a given harmonic frequency can be related to the eddy current phase of the fundamental frequency (or another harmonic) in terms of the harmonic index, where the harmonic index (i) equals 1, 2, 3, . . . , N. The eddy current phase as a function of the harmonic is as follows:

$$\phi_{Ei} = \frac{\pi}{2} - \arctan\left(\frac{\omega_i L}{R}\right) \quad (11)$$

where the angular frequency of the harmonic is defined as the harmonic index multiplied by the fundamental harmonic value or $$\omega_i = i\omega_l. \quad (12)$$

The eddy current phase of higher order harmonics can be related to the eddy current phase of the first harmonic using the following ratio:

$$\kappa_i \equiv \frac{\tan\left(\frac{\pi}{2}-\phi_{Ei}\right)}{\tan\left(\frac{\pi}{2}-\phi_{Ei}\right)} = i \quad (13)$$

Figure 5:
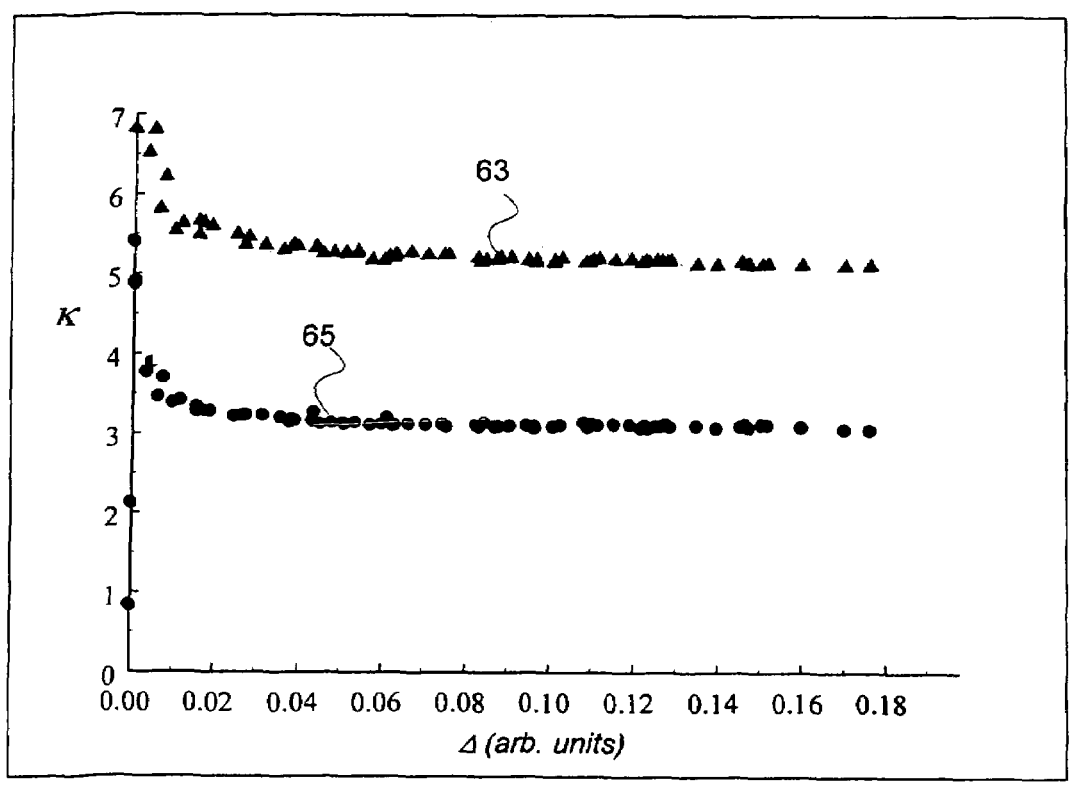
FIG. 5 shows experimental values of κ for the third and fifth harmonics when a stainless steel ring is used to disturb the signal of a stationary sensor.

This expression is confirmed experimentally as shown in FIG. 5. In FIG. 5, experimental values of $\kappa$ for i=3 (solid circles 65) and i=5 (solid triangles 63) are plotted as a function of $\Delta=|A_{T1}-A_{U1}|$. Each point represents a new position for the stainless steel ring. The sensor was stationary for the entire time of data collection.

The ratio relating the eddy current phases of two signals can be further generalized to any pair of harmonic or non-harmonic frequencies. This continuous form of $\kappa$ can be normalized to a particular frequency $\omega_n$ and written as follows:

$$\kappa(\omega) \equiv \frac{\tan\left(\frac{\pi}{2}-\phi_E\right)}{\tan\left(\frac{\pi}{2}-\phi_{En}\right)} = \frac{\omega}{\omega_n} \quad (14)$$

Figure 6:
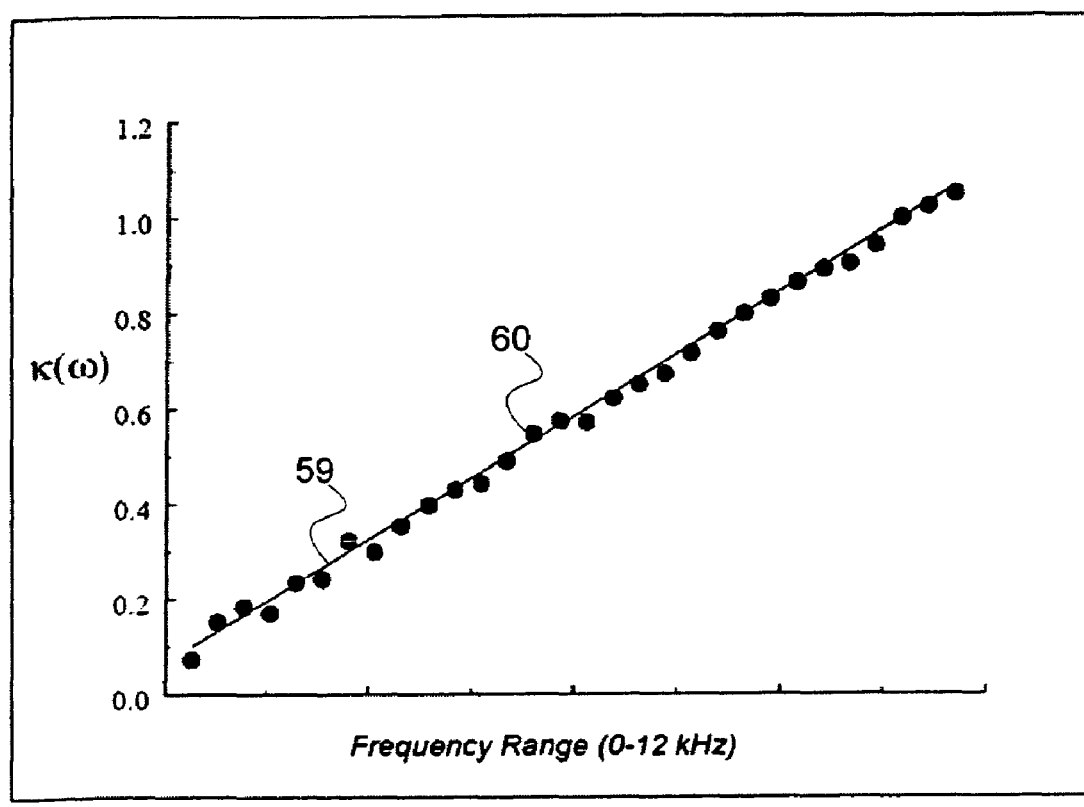
FIG. 6 shows experimental values of κ(ω) as a function of frequency for a sensor disturbed by a stainless steel ring.

This generalization is confirmed experimentally as shown in FIG. 6. In FIG. 6, theoretical values of $\kappa(\omega)$ (represented as a solid line 59) and experimental values for $\kappa$ (represented as solid circles 60) are shown as a function of $\omega$ for a stationary sensor with a signal disturbed by a stainless steel ring. Once the steel ring was in place, it was held stationary for the duration of the data collection (i.e., for the duration of the frequency sweep). The experimental values for $\kappa$ overlay the theoretical results, verifying the generalizations shown in equation (14). Further generalizations based on the use of various (e.g., non-harmonic) frequencies are described below.

The value of $\kappa(\omega)$ is used when solving a set of equations for two disturbed phasors. In the example that follows, the compensation procedure uses the phasors for the first and third harmonic. However, the theory applies to any pair or set of frequencies. The real and imaginary components of the fundamental frequency (first harmonic) are as follows:

$$Re_{T1}=A_{T1}\cos(\phi_{T1})=A_{U1}\cos(\phi_{U1})+A_{E1}\cos(\phi_{U1}+\phi_{E1}) \quad (15)$$

$$Im_{T1}=A_{T1}\sin(\phi_{T1})=A_{U1}\sin(\phi_{U1})+A_{E1}\sin(\phi_{U1}+\phi_{E1}) \quad (16)$$

The real and imaginary components of the third harmonic are as follows:

$$Re_{T3}=A_{T3}\cos(\phi_{T3})=A_{U3}\cos(\phi_{U3})+A_{E3}\cos(\phi_{U3}+\phi_{E3}) \quad (17)$$

$$Im_{T3}=A_{T3}\sin(\phi_{T3})=A_{U3}\sin(\phi_{U3})+A_{E3}\sin(\phi_{U3}+\phi_{E3}) \quad (18)$$

The left hand side of each expression (equation (15-18)) is the total sensor signal at a given position and orientation.

From the above expressions, in order to perform compensation, the undisturbed phase of each sensor signal must be input. It is generally assumed in the literature that $\phi_{Ui}$ is a constant throughout the measurement volume. The undisturbed phase, however, can be a function of sensor position and orientation (pose). For example, sensor poses for which the signal amplitude is small have different phase values than the "expected" large amplitude values (also referred to as asymptotic phase values). Therefore, the undisturbed phase is known to high precision if both the sensor pose is known and a model for the phase exists.

If the sensor pose is not known, an iterative process allows the compensation process to determine the actual undisturbed phase starting with asymptotic phase values, for large sensor signals. The solution for $\phi_{Ui}$ at each iteration can be used as a phase input for the eddy current compensation algorithm. The asymptotic values of the undisturbed phases can be determined at the time of system characterization. In a first order compensation scheme only the asymptotic $\phi_{Ui}$ values are used.

Figure 7:
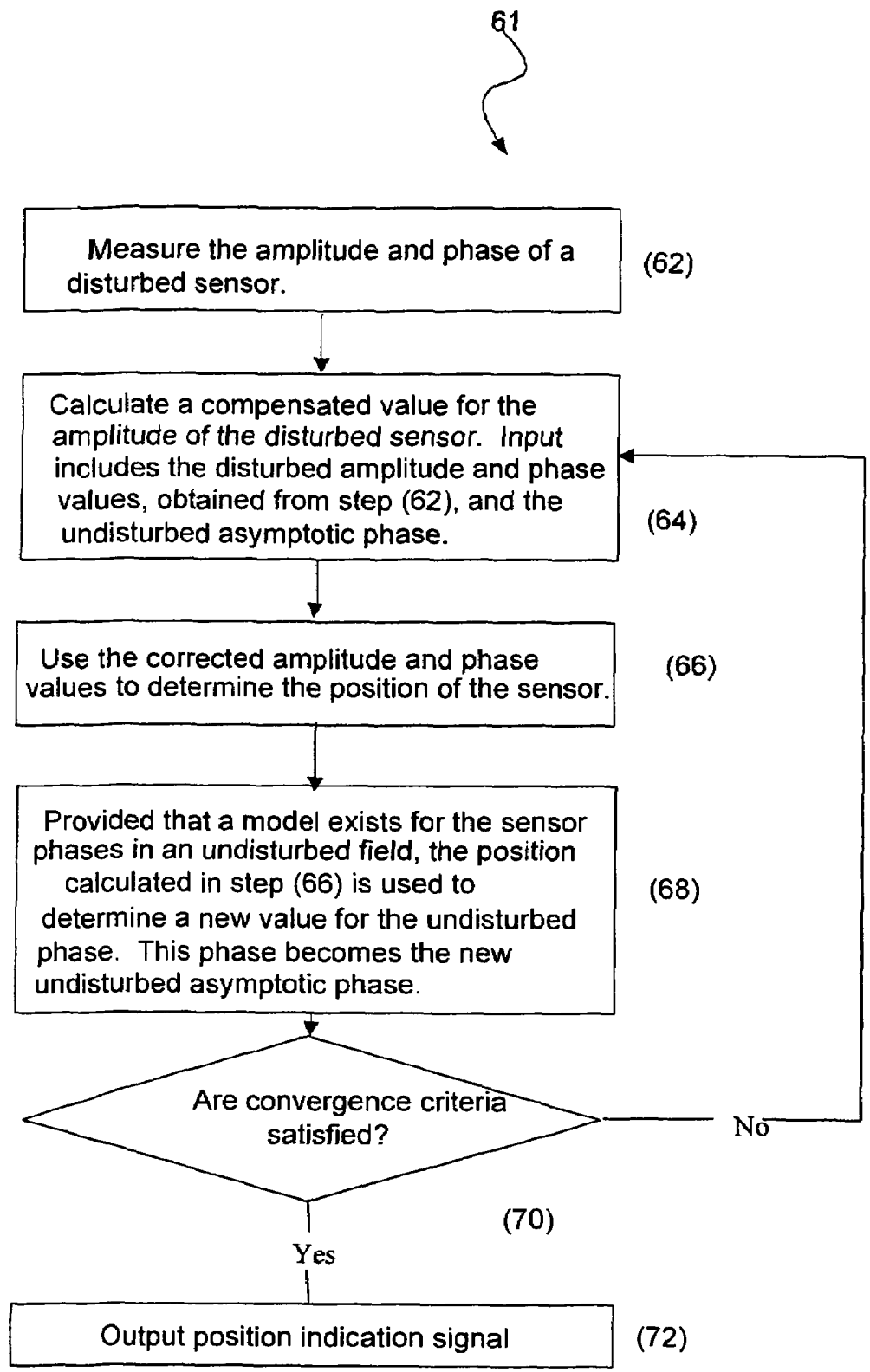
FIG. 7 is a flow chart of a process to determine an asymptotic undisturbed phase.

Referring to FIG. 7, a process 61 for measuring the amplitude and phase of a disturbed sensor is described. Using the disturbed amplitude and phase (step 62) a compensated value for the amplitude of the disturbed sensor is calculated (step 64). Inputs to this calculation include the disturbed amplitude, the disturbed phase, and the undisturbed asymptotic phase. Process 40 describes a compensation method that can be used in step 64 and an alternative compensation method is described below. The corrected amplitude and phase values are used to determine the position of the sensor (step 66). If a model exists for the sensor phases in an undisturbed field, the position calculated in step 66 is used to determine a new value for the undisturbed phase (step 68). This phase becomes the new undistorted asymptotic phase. Process 61 determines if position fit convergence criteria are met (step 70). If the criteria are met, the calculated position is accepted and the process outputs a position indication signal (step 72). If the criteria are not met, process 61 returns to calculating a compensated value with the new asymptotic phase. This process repeats until the compensation criteria are met (step 70).

Given that $A_T$ and $\phi_T$ are the total amplitude and phase of a sensor signal, and given that $\phi_U$ is a quantity that can be determined at the time of characterization of a system, the undisturbed amplitude (i.e. corrected) $A_U$ can be determined. The undisturbed phase may drift or vary during the lifetime of a system, and can be re-determined or refined real-time using an iterative process.

The value of an undisturbed ratio $F_i = A_{ui}/A_{u1}$, where i=1, 3, 5, . . . for the present discussion, is also needed to perform a compensation of the signal. For some waveforms such as a square wave or a triangular wave, the values of $F_i$ can be determined using Fourier analysis. In general, however, sensor waveforms are complex and the $F_i$ values must be determined at the time of system characterization. It is assumed that the $F_i$ values do not depend on sensor position and/or orientation (this can be verified at the time of system characterization). In addition to the measured $F_i$ value, the value of $\kappa_i$ calculated using equation (13) (or $\kappa(\omega)$ using equation (14)), expresses the eddy current phase of higher-order harmonics in terms of the eddy current phase of the first harmonic.

With the generalizations described above, a set of four equations (e.g., equations (15-18)) can be written in terms of four unknowns, namely: $A_{U1}$, $A_{E1}$, $A_{E3}$, and $\phi_{E1}$. A numerical method can be used to solve this system of equations. In one example, the data used as input to the model includes the real and imaginary components of the first and third harmonics of the total sensor signal.

Figure 8:
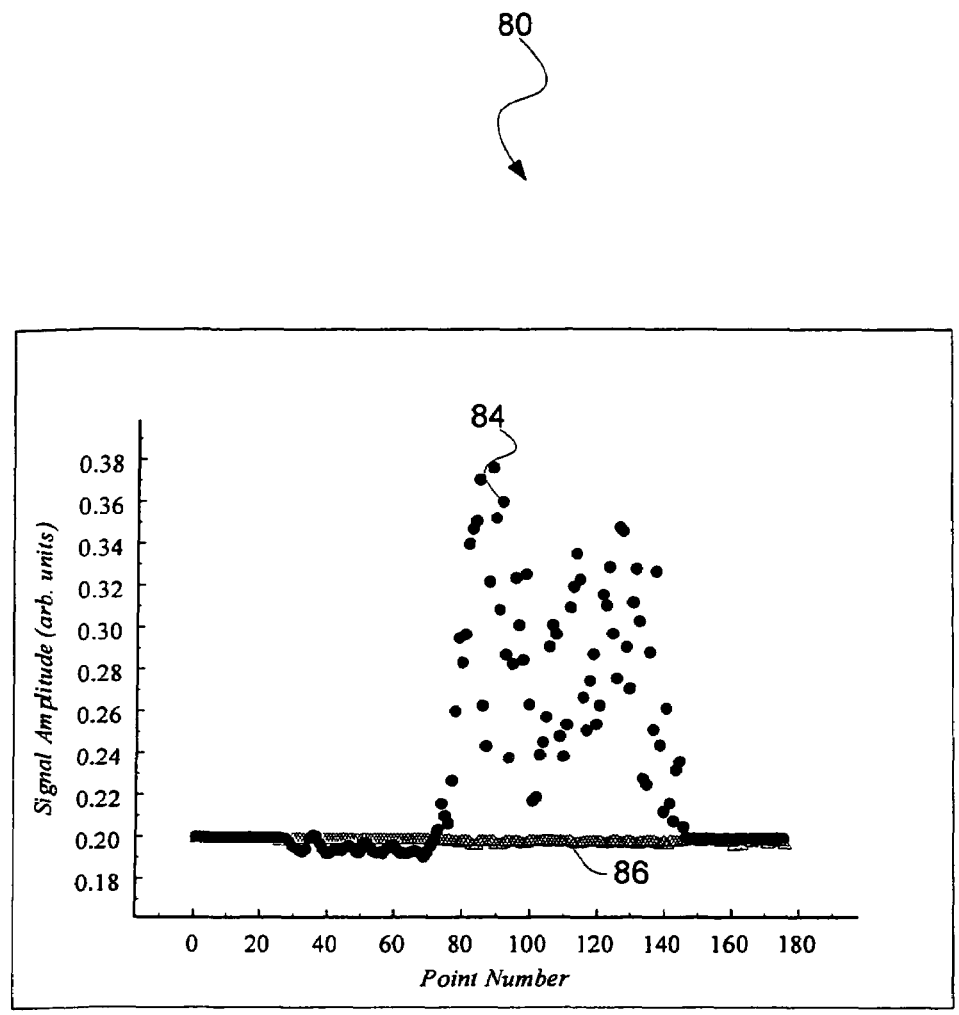
FIG. 8 shows an experimental result of the eddy current compensation.
Figure 9:
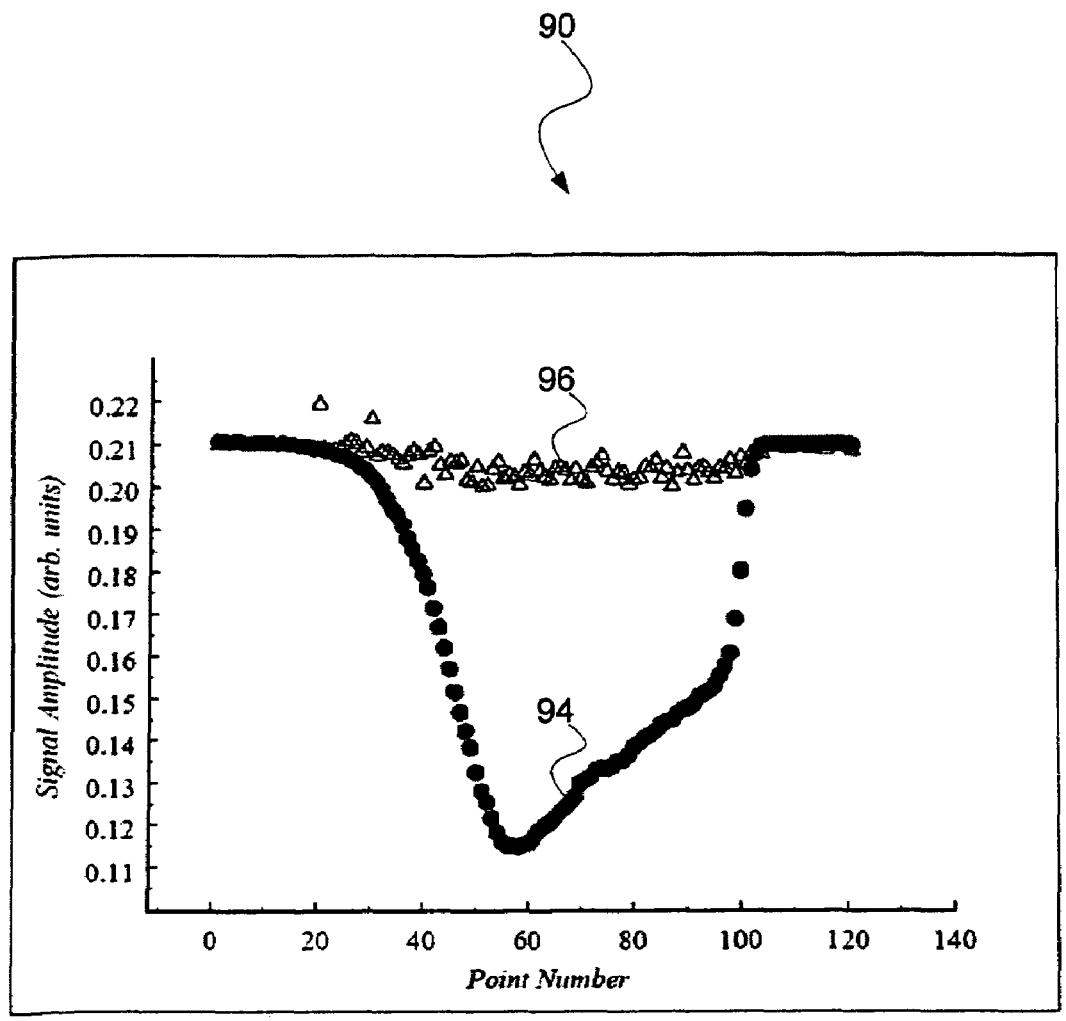
FIG. 9 shows an experimental result of the eddy current compensation.

FIGS. 8 and 9 show graphical representations of exemplary results from the eddy current compensation procedure. The results shown in these figures are for a field generator coil driven with a waveform having a fundamental frequency of about 3 kHz and a third harmonic of about 9 kHz. Higher order harmonics were present but were not used in the compensation scheme.

In FIG. 8, the signal strength of a stationary sensor 84 is disturbed as a large stainless steel ring is moved into the vicinity of the field generating coil and sensor. The solid circles 84 represent the signal before compensation and the open triangles 86 represent the signal after compensation.

In FIG. 9, the signal strength of a stationary sensor is disturbed as a stainless steel plate moved into and out of the vicinity of the field generating coil and sensor. The solid circles 94 represent the signal before compensation and the open triangles 96 represent the signal after compensation.

An alternative method of solving the system of equations presented in equation (15) through equation (18) is to work explicitly with the real and imaginary components of the sensor signals as follows:

$$\text{Re}_{T1} = \text{Re}_{U1} + \text{Re}_{E1} \quad (19)$$

$$\text{Im}_{T1} = \text{Im}_{U1} + \text{Im}_{E1} \quad (20)$$

$$\text{Re}_{T3} = \text{Re}_{U3} + \text{Re}_{E3} \quad (21)$$

$$\text{Im}_{T3} = \text{Im}_{U3} + \text{Im}_{E3} \quad (22)$$

$$\phi_{U1} = \arctan\left(\frac{\text{Im}_{U1}}{\text{Re}_{U1}}\right) \quad (23)$$

$$\phi_{U3} = \arctan\left(\frac{\text{Im}_{U3}}{\text{Re}_{U3}}\right) \quad (24)$$

$$F \equiv F_3 = \frac{\sqrt{\text{Re}_{U3}^2 + \text{Im}_{U3}^2}}{\sqrt{\text{Re}_{U1}^2 + \text{Im}_{U1}^2}} \quad (25)$$

$$\kappa \equiv \kappa_3 = \frac{\tan\left[\frac{\pi}{2} - \arctan\left(\frac{\text{Im}_{E3}}{\text{Re}_{E3}}\right) + \arctan\left(\frac{\text{Im}_{U3}}{\text{Re}_{U3}}\right)\right]}{\tan\left[\frac{\pi}{2} - \arctan\left(\frac{\text{Im}_{E1}}{\text{Re}_{E1}}\right) + \arctan\left(\frac{\text{Im}_{U1}}{\text{Re}_{U1}}\right)\right]} = 3 \quad (26)$$

A numerical method can be used to solve the above identified set of equations, however, a closed form solution does exist and may be used. For example, in the closed form solution, the amplitude of the fundamental harmonic $A_{U1}$ can be represented as:

$$A_{U1} = |\text{Re}'_{U1}| = \left|-\frac{\kappa \text{Re}'_{T1} \text{Im}'_{T3} - \text{Re}'_{T3} \text{Im}'_{T1}}{F \text{Im}'_{T1} - \kappa \text{Im}'_{T3}}\right| \quad (27)$$

where $$\begin{pmatrix} \text{Re}'_{Ti} \\ \text{Im}'_{Ti} \end{pmatrix} = \begin{pmatrix} \cos\phi_{Ui} & \sin\theta_{Ui} \\ -\sin\phi_{Ui} & \cos\phi_{Ui} \end{pmatrix} \begin{pmatrix} \text{Re}_{Ti} \\ \text{Im}_{Ti} \end{pmatrix}; i = 1, 3 \quad (28)$$

While in the above examples harmonic frequencies have been used to perform signal compensation, the process can be generalized to use any pair of frequencies (harmonic or non-harmonic frequencies).

In addition to providing compensation to a position indication signal for the presence of conductive objects near the magnetic tracking system as described above, the presence of conductive objects can also be detected by monitoring the ratio $A_{T3}/A_{T1}$ and noting deviations from $F_3$.

Alternatively, to detect the presence of conductive objects one can monitor deviations from $\phi_{Ui}$ for large amplitude signals and regard phase changes to be associated with the presence of conductive objects. In another method, the real and imaginary components at each frequency are monitored. Any number of mathematical techniques can then be used to differentiate between real and imaginary components in undisturbed and disturbed environments.

As described above, the κ can be generalized as shown in equation (14), reproduced to follow:

$$\kappa(\omega) \equiv \frac{\tan\left(\frac{\pi}{2} - \phi_E\right)}{\tan\left(\frac{\pi}{2} - \phi_{En}\right)} = \frac{\omega}{\omega_n} \tag{14}$$

This can be rewritten as:

$$\kappa_{ij} \equiv \kappa(\omega_i) = \frac{\omega_i}{\omega_j} \tag{29}$$

where the indices i=1, ..., N and j=1, ..., N label the frequencies for which sensor amplitudes have been measured, and N is the total number of frequencies for which measurements are performed. These indices can be any frequency and are not necessarily harmonic labels. The exact nature of the frequency spectrum depends on the hardware of the system and on the waveform driving the field generator coils. The $j^{th}$ frequency is used as a "normalization" frequency (labeled as 1 in equation (13) for example)

Equation (27) can also be generalized to any pair of frequencies as follows:

$$A_{Uij} = \left| -\frac{\kappa_{ij} \text{Re}'_{Tj} \text{Im}'_{Ti} - \text{Re}'_{Ti} \text{Im}'_{Tj}}{F_{ij} \text{Im}'_{Tj} - \kappa_{ij} \text{Im}'_{Ti}} \right| \tag{30}$$

where $$\begin{pmatrix} \text{Re}'_{Ti} \\ \text{Im}'_{Ti} \end{pmatrix} = \begin{pmatrix} \cos\phi_{Ui} & \sin\phi_{Ui} \\ -\sin\phi_{Ui} & \cos\phi_{Ui} \end{pmatrix} \begin{pmatrix} \text{Re}_{Ti} \\ \text{Im}_{Ti} \end{pmatrix} \tag{31}$$

for all i. Although equation (30) is explicitly written for pairs of frequencies, any number of relevant mathematical formulations that are stated in terms of the real and imaginary values can be used for compensation. For example, for continuous frequency functions, a complex polynomial can be fit to a characteristic undisturbed sensor signal. Changes in the expected polynomial coefficients of subsequent measurements can be used to indicate the presence of conductive objects. Adjustments to these polynomial coefficients can then be made to compensate for any distortions of a disturbed frequency function. A proper propagation of errors for the real and imaginary values of equations (30) and (31) can also be performed to account for small amplitude signals and measurement uncertainties.

Given the above equations, the signal of the $j^{th}$ frequency can be corrected based on the real and imaginary values of the $i^{th}$ frequency. Each $j^{th}$ frequency therefore has N−1 corrected values, from which one can calculate a weighted average amplitude, $S_j$, (or real and imaginary components) and standard deviation $\Delta S_j$ (e.g. uncertainty).

The next step in this compensation procedure is to calculate a $\chi^2$ value as follows:

$$\chi^2 = \sum_{j=1}^{N} \frac{(a\overline{S}_j - S_j)^2}{(\Delta S_j)^2} \tag{32}$$

where 'a' is the amplitude used in a position fit and $\overline{S}_j$ is the expected and normalized amplitude, for frequency j of an undisturbed frequency function, obtained from a field generator characterization process (in an undisturbed environment). From the minimizing condition $$\frac{d\chi^2}{da} = 0 \tag{33}$$

the desired amplitude 'a' can be determined as follows:

$$a = \frac{\sum_{j=1}^{N} \frac{(\overline{S}_j S_j)}{(\Delta S_j)^2}}{\sum_{j=1}^{N} \frac{(\overline{S}_j)^2}{(\Delta S_j)^2}} \tag{34}$$

The $\chi^2$ value can also be used to detect the presence of conductive objects. This is done by calculating 'a' for a set of frequency amplitudes (or real and imaginary signal components) that have not been corrected. The resulting value of 'a' is then substituted into equation (32) and a $\chi^2$ value is computed.

Figure 10:
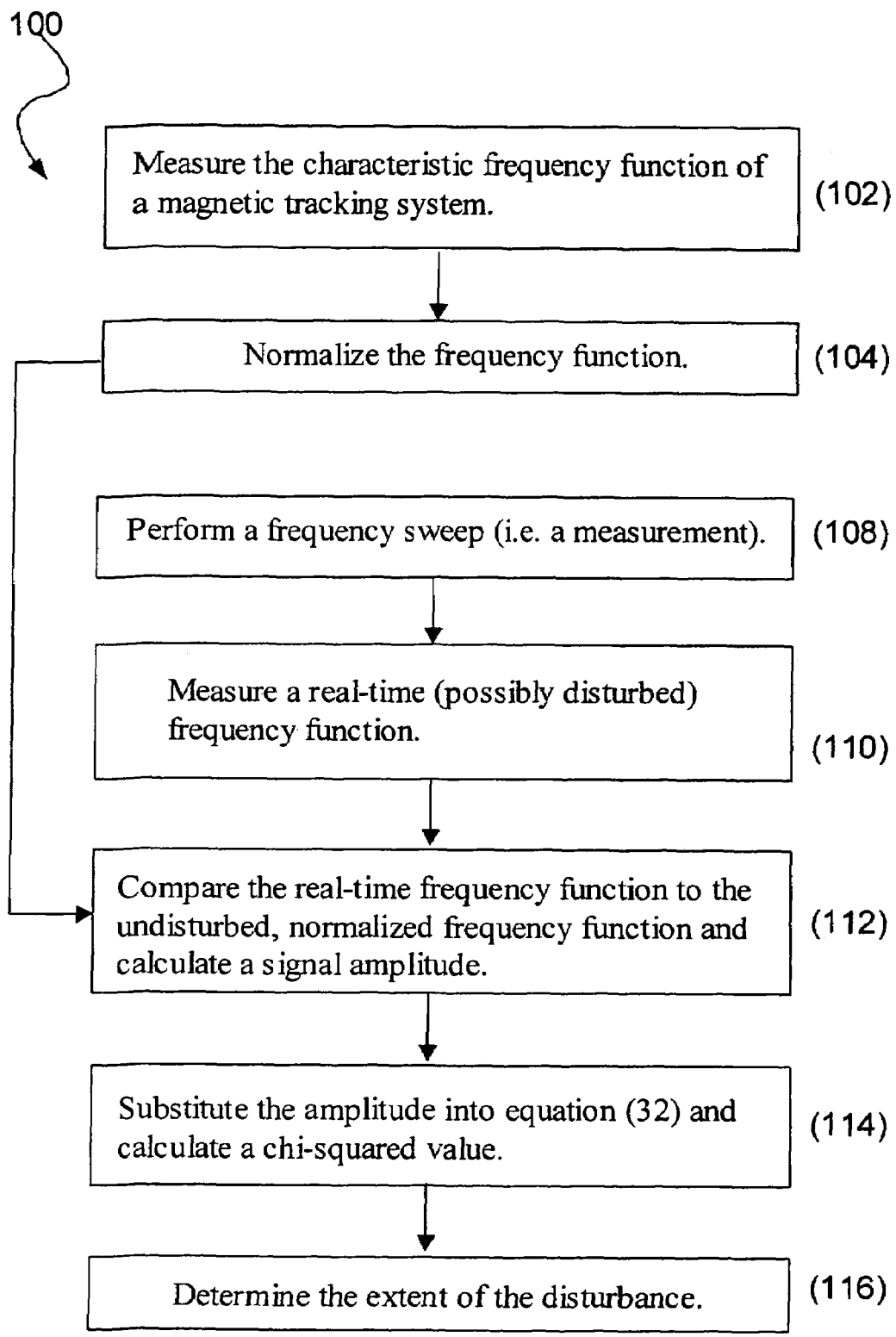
FIG. 10 is a flow chart of a process to determine the presence of a disturbance based on a chi-squared value.

Referring to FIG. 10, a process 100 for eddy current detection is achieved through monitoring the value of $\chi_2$. Appropriate thresholds can be set on $\chi^2$ to indicate different levels of distortion. Process 100 is a two stage process. In the first stage (steps 102 and 104) the compensation system measures the characteristic frequency function of a magnetic tracking system in an undisturbed field (step 102) and normalizes the function (step 104). For example, the function can be normalized by setting the area under the function to unity. This stage can be achieved during the time of system characterization. The second stage of process 100 (steps 108, 110, 112, 114, and 116) occurs when the system is in real-time operation and a disturbance is near the system. During this time the system performs a frequency sweep (step 108) and measures a real-time, and possibly disturbed, frequency function (step 110). The real-time frequency function is then compared to the undisturbed, normalized frequency function and the amplitude ('a') is calculated according to equation (34) (step 112). The calculated amplitude is substituted into equation (32) and a value for $\chi^2$ is calculated (step 114). The $\chi^2$ value is used to determine the extent of the disturbance to the system (step 116). In general, a small value of $\chi^2$ indicates a small disturbance and a large value of $\chi^2$ indicates a large disturbance.

Figure 11:
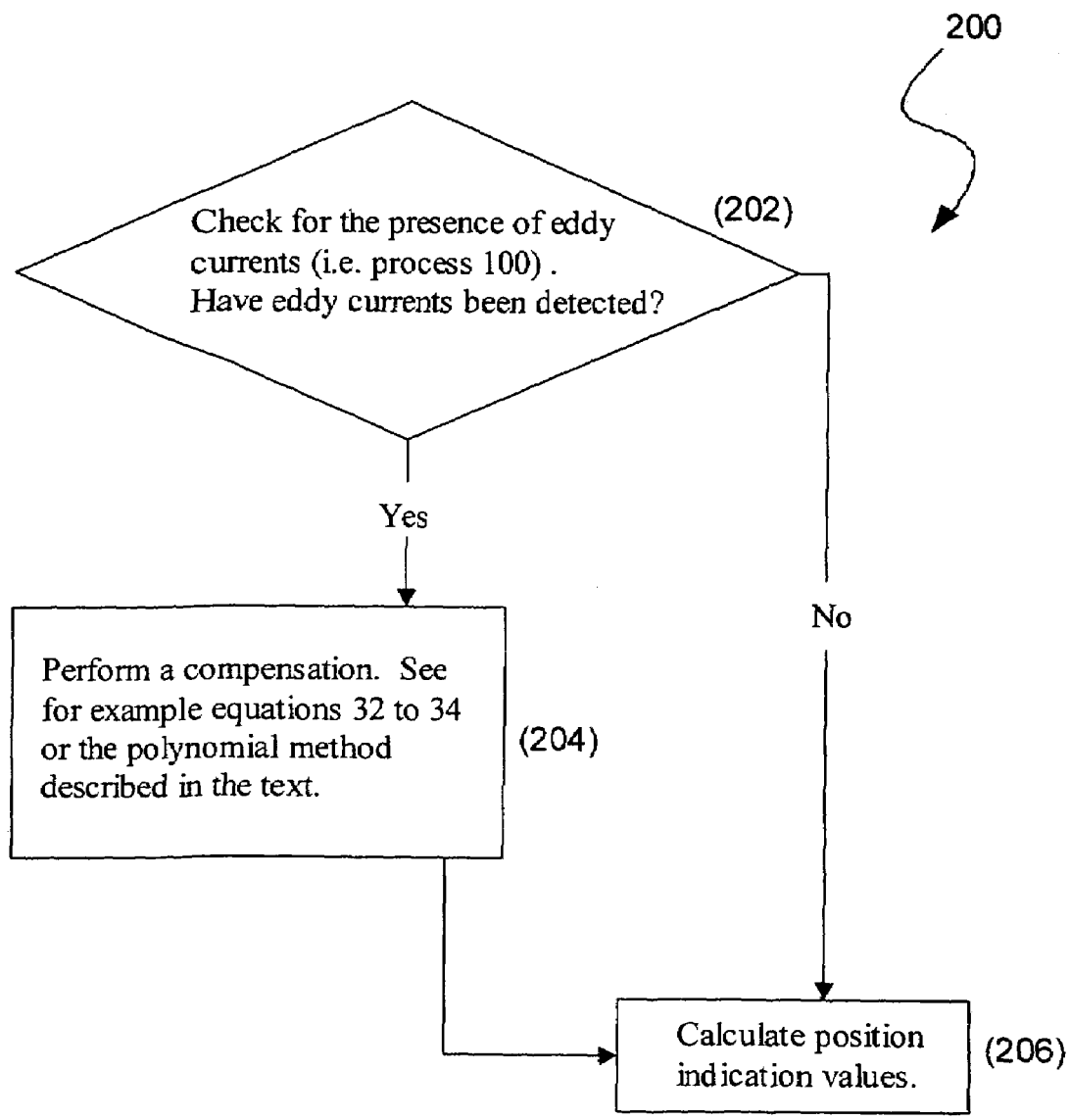
FIG. 11 is a flow chart of a signal compensation process.

Referring to. FIG. 11, a process 200 describes a method for determining position indication values. This process begins with eddy current detection(step 202), for example, process 100. If eddy currents are detected then a compensation (step 204) is performed prior to calculating position indication values (step 206), otherwise the process can proceed immediately to calculating position indication values (step 206)

Multiple field generator-coils (e.g., 2, 4, 8, 12 . . . ) may be included in a detection scheme. Multiple coils provide the advantage of increased sensitivity and redundancy. The presence of conductive objects can cause a signal disturbance due to coupling to one or more of the field generator and/or sensor coils.

The $\chi^2$ value can also be used to aid in "tuning" the system to a particular frequency range such that sensitivity to different types of conductive objects is obtained. For example, stainless steel objects are often more easily detected in a mid-frequency range while aluminum objects are more easily detected in a low-frequency range. Other factors such as the geometry of the object can also affect the region of sensitivity. Once the region of sensitivity has been determined for a particular conductive object, equation (34) can be used in the less sensitive regions (e.g. low-frequency ranges) to obtain a value of '$\alpha$'. The motivation for doing this comes from the realization that conductive objects can be modeled as low-pass R-L circuits (i.e. filters).

A number of embodiments of the invention have been described. Nevertheless, it will be understood that various modifications may be made without departing from the spirit and scope of the invention. Accordingly, other embodiments are within the scope of the following claims.

What is claimed is:

1. A method for detecting the presence of conductive objects, the method comprising:
    determining a characteristic frequency function of an undisturbed magnetic tracking system;
    measuring a disturbed real-time frequency function;
    calculating real and imaginary components of the position indication signal using a chi-squared minimization of the disturbed frequency function to the undisturbed frequency function;
    calculating a chi-squared value based on the characteristic frequency function and the disturbed frequency function; and
    monitoring the chi-squared value to detect changes indicating the presence of a conductive object.

2. The method of claim 1 wherein determining the characteristic frequency function includes determining the characteristic frequency function based on undisturbed position indication signals.

3. The method of claim 1 further comprising monitoring the chi-squared value for a plurality of position indication signals.

4. The method of claim 3 wherein detecting a change in the chi-squared value of at-least one of the plurality of position indication signals indicates the presence of conductive objects.

5. The method of claim 1 further comprising determining, calculating, and monitoring the chi-squared value for a plurality of frequencies.

6. The method of claim 5 wherein the detection of a change in a chi-squared value at a particular frequency range can indicate the presence of a particular type of conductive objects.

7. The method of claim 6 wherein the particular frequency range is a mid-frequency range.

8. The method of claim 6 wherein the particular frequency range is a low-frequency range.

9. The method of claim 6 wherein the particular frequency range is a high-frequency range.

10. The method of claim 6 further comprising determining the position indication signal in a frequency range that is not affected by a particular type of conductive object.

11. A system for detecting the presence of conductive objects, the system being configured to:
    determine a characteristic frequency function of an undisturbed magnetic tracking system;
    measure a disturbed real-time frequency function;
    calculate real and imaginary components of the position indication signal using a chi-squared minimization of the disturbed frequency function to the undisturbed frequency function;
    calculate a chi-squared value based on the characteristic frequency function and the disturbed frequency function; and
    monitor the chi-squared value to detect changes indicating the presence of a conductive object.

12. The system of claim 11 wherein the system is further configured to determine the characteristic frequency function based on undisturbed position indication signals.

13. The system of claim 11 wherein the system is further configured to monitor the chi-squared value for a plurality of position indication signals.

14. The system of claim 11 wherein the system is further configured to determine, calculate, and monitor the chi-squared value for a plurality of frequencies.

15. The system of claim 11 wherein the system is further configured to determine the position indication signal in a frequency range that is not affected by a particular type of conductive object.

* * * * *